(12) United States Patent
Pierard

(10) Patent No.: US 6,482,826 B1
(45) Date of Patent: Nov. 19, 2002

(54) METHOD OF TREATING ALOPECIA

(75) Inventor: Gérald E. Pierard, Angleur (BE)

(73) Assignee: Janssen Pharmaceutica N.v., Beerse (BE)

( * ) Notice: Subject to any disclaimer, the term of this patent is extended or adjusted under 35 U.S.C. 154(b) by 0 days.

(21) Appl. No.: 08/437,472

(22) Filed: May 9, 1995

Related U.S. Application Data

(63) Continuation of application No. 08/192,934, filed on Feb. 7, 1994, now abandoned, which is a continuation of application No. 07/952,624, filed on Nov. 25, 1992, now abandoned.

(30) Foreign Application Priority Data

Jun. 26, 1990 (GB) .............................................. 9014221
Jun. 19, 1991 (WO) ................................ PCT/EP91/01136

(51) Int. Cl.$^7$ .............................................. A61K 31/50
(52) U.S. Cl. ................................................... 514/254.07
(58) Field of Search ............................ 514/252, 254.07

(56) References Cited

U.S. PATENT DOCUMENTS

| | | | |
|---|---|---|---|
| 4,335,125 A | * 6/1982 | Heeres et al. ................ | 424/250 |
| 4,569,935 A | * 2/1986 | Rosenberg et al. .......... | 514/252 |
| 4,942,162 A | * 7/1990 | Rosenberg et al. .......... | 514/252 |
| 5,204,337 A | * 4/1993 | Labrie et al. ................ | 514/182 |
| 5,374,633 A | * 12/1994 | Parab .......................... | 514/252 |
| 5,476,852 A | * 12/1995 | Cauwenbergh .............. | 514/252 |

OTHER PUBLICATIONS

Embase Abstract No. 83240235, 1983, Hanna, J.M., et al.*

*Illustrated Stedman's Medical Dictionary* (24$^{th}$ Ed.), Williams and Wilkins, 1982, Baltimoree, MD., p. 1090.*

Kovács et al., "Usefulness of Ketoconazole (Nizoral) in the Treatment of Androgenization . . . ", Ther.Hung. 36/4 (174–178), 1988.*

* cited by examiner

Primary Examiner—Minna Moezie
Assistant Examiner—San Hui

(57) ABSTRACT

Method of treating individuals with alopecia or having inferior quality hair, by administering to the scalp of said individuals an effective amount of ketoconazole. Novel compositions comprising as an active ingredient ketoconazole and an inert carrier.

8 Claims, No Drawings

METHOD OF TREATING ALOPECIA

CROSS REFERENCE TO RELATED APPLICATIONS

This is a continuation, of application Ser. No. 08/192,934, filed Feb. 7, 1994, now abandoned, which is a continuation of copending application Ser. No. 07/952,624, filed on Nov. 25, 1992, now abandoned, which is based on PCT Application No. PCT/EP 91/01136, filed Jun. 19, 1991, which claims priority from Great Britain Application Serial No. 90.14.221.7, filed Jun. 26, 1990.

A healthy, thick and uniform hair growth on the scalp is generally considered an important aesthetic aspect of the human body. The loss of hair or any imperfection in the quality of the hair is consequently often experienced a very undesirable feature of one's physical appearance.

The fact that a majority of the male population is genetically predisposed to lose progressively its hair and the knowledge that current modes of treatment are very few, with a low number of individuals effectively responding to the treatment, more than amply illustrate the scope and magnitude of the problems involved and the need for additional therapies effective in reversing, arresting or retarding loss of hair and improving the quality of hair.

It has now been found that ketoconazole can effectively reverse, arrest or retard the loss of hair as experienced in alopecia and further, that ketoconazole does have a beneficial effect on the quality of hair.

The present invention is concerned with a method of treating individuals suffering from alopecia, said method comprising administering to said individuals the compound ketoconazole or a pharmaceutically acceptable acid addition salt thereof, in an amount effective in reversing, arresting or retarding said alopecia. Further, the present invention also is concerned with a method of treating individuals having an inferior quality of hair, said method comprising administering to said individuals the compound ketoconazole or a pharmaceutically acceptable acid addition salt thereof, in an amount effective in ameliorating the quality of hair.

Ketoconazole as mentioned hereinabove is the generic name of the compound (±)-cis-1-acetyl-4-[4-[[2-(2,4-dichlorophenyl)-2-(1H-imidazol-1-ylmethyl)-1,3-dioxolan-4-yl]methoxy]phenyl]piperazine, which may be represented by the formula.

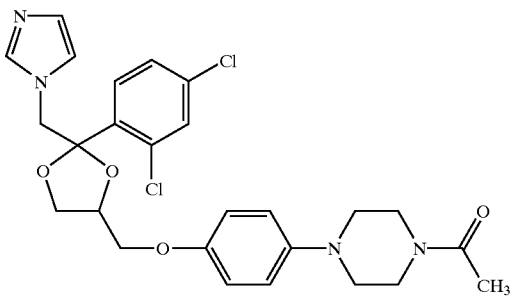

The compound ketoconazole used in the method of the present invention is a known antifungal agent and its preparation as well as its pharmacological properties are described in U.S. Pat. No. 4,335,125.

The compound ketoconazole can be used as such or in a pharmaceutically acceptable acid addition salt form, the latter being conveniently obtained by treating the base form with an appropriate acid. Appropriate acids comprise, for example, inorganic acids such as hydrohalic acids, e.g. hydrochloric or hydrobromic acid; sulfuric acid; nitric acid; phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy- 1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. The term acid addition salt form as used hereinabove also comprises the solvates which the compound ketoconazole and its acid addition salts are able to form. Examples of such solvates are e.g. the hydrates, alcoholates and the like.

The term alopecia as used herein is meant to comprise the loss of hair from the scalp but also from the beard in humans. More in particular, the term alopecia relates to androgenetic alopecia or male pattern alopecia (baldness) which is characterized by the progressive, diffuse, symmetrical loss of hair from the scalp, typically starts at the frontal end of the scalp and gradually spreads to the vertex, ultimately leaving only a sparse peripheral band of hair covering the temples and occiput.

Since alopecia is a condition which at present can hardly be treated at all, the present finding that ketoconazole may effectively be employed in treating individuals suffering from alopecia, more in particular individuals with early androgenetic alopecia, is surprising. In this regard the term effectively means that treatment with ketoconazole results in the reversal, the arrest or the retardation of loss of hair and in the improvement of the quality of hair, in particular of the thickness of hair as can be gauged by measuring the calibre of the hairs. The term early androgenetic alopecia means male pattern baldness classified as type I, II, III, IV or V on the Hamilton scale.

The term quality of hair as used herein relates to desirable physical properties of hair such as strength, thickness, density, uniformity and sensibility of hair. Inferior strength may manifest itself, for example, by splitting or by breaking. The thickness of a hair most commonly is expressed by its diameter or calibre. Density is meant to define the number of hairs per unit area, whereas uniformity relates to the constancy or gradual change of said density in contiguous areas of the scalp. Sensibility of hair refers to the presence of tactile sense in hair.

The compound ketoconazole and its acid addition salts used in the methods of the present invention are most preferably applied to the affected areas of the scalp or beard in the form of appropriate compositions, in particular compositions usually employed for the topical administration of drugs or cosmetic compositions. Said compositions contain the active ingredient ketoconazole, preferably in a 0.1 to 5% concentration (weight by volume), and any known dermatologically acceptable carrier and may take a wide variety of forms such as, for example, liquid forms, e.g. solutions, or suspensions in aqueous or oily mediums; or semi-liquid formulations, e.g. creams, hydrogels, gels, pastes, ointments, salves, tinctures and the like.

Other such compositions are preparations of the cosmetic type, such as toilet waters, packs, lotions, skin milks or milky lotions and shampoos. Said preparations contain, besides the active ingredient ketoconazole, components usually employed in such preparations. Examples of such components are oils, fats, waxes, surfactants, humectants, penetration enhancing agents, thickening agents, lipid absorbents, anti-oxidants, viscosity stabilizers, chelating agents, buffers, preservatives, perfumes, dyestuffs, lower alkanols, and the like. If desired, further active ingredients may be incorporated in the compositions, e.g. antiinflammatory agents, antibacterials, antifungals, disinfectants, vitamins, sunscreens, antibiotics or anti-dandruff agents. Interesting compositions for use in the methods according to the present invention are lotions and shampoos, typically containing from 0.2 to 2.5%, in particular 2% ketoconazole.

The lotions mentioned hereinabove are novel and have been especially developed for use in the methods of the present invention. Typically such lotions comprise 0.2 to 2.5%, in particular about 2% (w/v) of the active ingredient ketoconazole; propylene carbonate in an amount of from 20 to 40%, in particular from 20 to 30%, more in particular about 25% (w/v); ethanol in an amount of from 25 to 55% in particular from 25 to 35%, more in particular about 28% (w/v); optionally any other components as defined hereinabove and usually employed in similar compositions; the remainder of the lotion being water.

Particular instances of the aforementioned preparations are those which comprise a cyclodextrin or a derivative thereof. Said cyclodextrin or derivative thereof defines the topically acceptable unsubstituted and substituted cyclodextrins known in the art, in particular $\alpha$-, $\beta$- or $\gamma$-cyclodextrins and the derivatives thereof, such as ethers, polyethers, mixed ethers.

To prepare said cyclodextrin based formulations, ketoconazole is added to a solution of the cyclodextrin in water, preferably under vigorous stirring, and then adding the remainder of the ingredients. In the final compositions the amount of cyclodextrin is about 2 to 40%, in particular about 2.5 to 25%, more in particular about 5 to 20%.

Other particular compositions for use in the methods of the present invention are those wherein the active ingredient ketoconazole is formulated in liposome-containing compositions. Different types of liposomes may be employed such as coarse (multilayer) liposomes or unilamellar liposomes and the like, which are formed, for example, with phosphatidyl cholines, ethanolamines, serines, sphingomyelins, cardiolipins, plasmalogens, phosphatidic acids, cerebiosides and the like. The viscosity of the liposomes can be increased by addition of one or more thickening agents such as xanthan gum, hydroxypropyl cellulose, hydroxypropyl methyl cellulose and mixtures thereof. The aqueous component may consist of water optionally in admixture with electrolytes, buffers and other ingredients such as preservatives. Preferred electrolytes are calcium, sodium and potassium chloride. The organic component may consist of a solvent such as ethanol, glycerol, propylene glycol, a polyethylene glycol and a suitable phopholipid such as, lecithin, phosphatidyl choline, phosphatidyl ethanolamine, phosphatidyl serine, phosphatidyl inositol, lysophosphatidyl choline, phosphatidyl glycerol and the like. Other lipofilic additives which may be added to selectively modify the characteristics of the liposomes are, e.g. stearylamine, phosphatidic acid, tocopherol, cholesterol, lanolin and the like.

For preparing ointments, creams, toilet waters, skin milks, and the like, typically from 0.1 to 10% in particular from 0.1 to 5% and more in particular from 0.2 to 2.5% of the active ingredient ketoconazole optionally in an acid addition form, is combined in intimate admixture with a skin-and-hair acceptable carrier. For the ease of preparing high-quality compositions finely divided particles, preferably micronized particles of the active ingredient ketoconazole and optionally of other solid components, are employed. In ointments or creams, the carrier for example consists of 1 to 20%, in particular 5 to 15% of a humectant, 0.1 to 10% in particular from 0.5 to 5% of a thickener and water, or said carrier may consist of 70 to 99%, in particular 20 to 95% of a surfactant, and 0 to 20%, in particular 2.5 to 15% of a fat; or 80 to 99.9% in particular 90 to 99% of a thickener, or 5 to 15% of a surfactant, 2–15% of a humectant, 0 to 80% of an oil, very small (<2%) amounts of preservative, colouring agent and/or perfume, and water. In a toilet water, the carrier for example consists of 2 to 10% of a lower alcohol, 0.1 to 10% or in particular 0.5 to 1% of a surfactant, 1 to 20%, in particular 3 to 7% of a humectant, 0 to 5% of a buffer, water and small amounts (<2%) of preservative, dyestuff and/or perfume. In a skin milk, the carrier typically consists of 10–50% of oil, 1 to 10% of surfactant, 50–80% of water and 0 to 3% of preservative and/or perfume. Other active ingredients may be incorporated at doses ranging from 0.005% to 0.5%, particularly from 0.01% to 0.1%. In the aforementioned preparations, all % symbols refer to weight by weight percentage. The humectant, surfactant, oil, other active ingredient, etc . . . referred to in said preparations may be any such component used in the pharmaceutical or cosmetic arts. Further, when in the above compositions one or more of the components make up the major part of the composition, the other ingredients can evidently be not present at their indicated maximum concentration and therefore will make up the remainder of the composition.

In many of the foregoing compositions it is advantageous to use micronized forms of ketoconazole, i.e. material having an average particle size of less than 10 microns since the high surface area will facilitate the dissolution.

The liquid fomulations mentioned hereinbefore may be packaged advantageously in any dosage dispensing device adapted for topical administration. In particular the present formulations, and especially the novel lotions described hereinabove may be applied as aerosols, e.g. by using an inert compressed gas as a propellant such as nitrogen or carbon dioxide, or alternatively by using a pump spray.

A preferred device for use according to the present invention comprises an atomizer or sprayer comprising a lotion as defined herinabove and carbon dioxide as a propellant.

In still a further aspect of the present invention there is provided the use of the compound ketoconazole as defined above, for the manufacture of a medicament for reversing, arresting or retarding alopecia, or for improving the quality of hair.

The ketoconazole containing compositions are applied topically to the area to be treated at regular intervals, as needed or convenient, e.g. at each washing occasion or thereafter. The duration of the treatment will depend upon the nature, extent and severity of the condition to be treated, as well as the frequency of application of the composition. No special precautions are needed other than those typical precautions which normally apply when administering drugs to the skin or hair.

EXAMPLES

A. Composition Examples

Example 1
Ketoconazole 2% Cream

| | |
|---|---|
| ketoconazole | 20 mg |
| propylene glycol | 200 mg |
| stearyl alcohol | 75 mg |
| cetyl alcohol | 20 mg |
| sorbitan monostearate | 20 mg |
| polysorbate 60 | 15 mg |
| isopropyl myristate | 10 mg |
| sodium sulfite anhydrous | 2 mg |
| polysorbate 80 | 1 mg |
| purified water | q.s. ad 1 g |

Stearyl alcohol, cetyl alcohol, sorbitan monostearate and isopropyl myristate are introduced into a doublewall jacketed vessel and heated until the mixture has completely molten. This mixture is added to a separately prepared mixture of purified water, propylene glycol and polysorbate 60 having a temperature of 70 to 75° C. while using a homogenizer for liquids. The resulting emulsion is allowed to cool to below 25° C. while continuously mixing. A solution of ketoconazole, polysorbate 80 and purified water and a solution of sodium sulfite anhydrous in purified water are next added to the emulsion while continuously mixing. The cream is homogenized and filled into suitable tubes.

Example 2
2% Topical Gel

| | |
|---|---|
| ketoconazole | 20 mg |
| hydroxypropyl β-cyclodextrine | 200 mg |
| propylene glycol | 50 mg |
| ethyl alcohol 95% (v/v) | 50 mg |
| carrageenan PJ | 10 mg |
| hydrochloric acid | q.s. until solution |
| sodium hydroxide | q.s. ad pH 6.0 |
| purified water | q.s. ad 1 g. |

Method of Preparation

To a solution of hydroxypropyl β-cyclodextrine in purified water is added ketoconazole while stirring. Hydrochloric acid is added until complete solution and then sodium hydroxide is added until pH 6.0. This solution is added to a dispersion of carrageenan PJ in propylene glycol while mixing. While mixing slowly the mixture is heated to 50° C. and allowed to cool to about 35° C. whereupon the ethyl alcohol is added. The rest of the purified water is added and the mixture is mixed until homogeneous.

Example 3
2% Topical Cream

| | |
|---|---|
| ketoconazole | 20 mg |
| hydroxypropyl β-cyclodextrine | 200 mg |
| mineral oil | 100 mg |
| stearyl alcohol | 20 mg |
| cetyl alcohol | 20 mg |
| glycerol monostearate | 20 mg |
| glycerol | 50 mg |
| sorbate 60 | 15 mg |
| polysorbate 60 | 35 mg |
| hydrochloric acid | q.s. until solution |
| sodium hydroxide | q.s. ad pH 6.0 |
| purified water | q.s. ad 1 g. |

Method of Preparation

To a solution of hydroxypropyl β-cyclodextrine in purified water is added ketoconazole while stirring. Hydrochloric acid is added until complete solution and next sodium hydroxide is added until pH 6.0. While stirring, glycerol and polysorbate 60 are added and the mixture is heated to 70° C. The resulting mixture is added to a mixture of mineral oil, stearyl alcohol, cetyl alcohol, stearyl monostearate and sorbate 60 having a temperature of 70° C. while mixing slowly. After cooling down to below 25° C., the rest of the purified water is added and the mixture is mixed until homogeneous.

Example 4
2% Liposome Formulation

| | |
|---|---|
| ketoconazole microfine | 2 g |
| phosphatidyl choline | 20 g |
| cholesterol | 5 g |
| ethyl alcohol | 10 g |
| methyl paraben | 0.2 g |
| propyl paraben | 0.02 g |
| disodium edetate | 0.15 g |
| sodium chloride | 0.3 g |
| hydroxypropylmethylcellulose | 1.5 g |
| purified water | ad 100 g |

Method of Preparation

A mixture of ketoconazole microfine, phosphatidyl choline, cholesterol and ethyl alcohol is stirred and heated at 55–60° C. until complete solution and is added to a solution of methyl paraben, propyl paraben, disodium edetate and sodium chloride in purified water while homogenizing. Hydroxypropylmethylcellulose in purified water is added and the mixing is continued until swelling is complete.

Example 5
2% Liposome Formulation

| | |
|---|---|
| ketoconazole microfine | 2 g |
| phosphatidyl choline | 10 g |
| cholesterol | 1 g |
| ethyl alcohol | 7.5 g |
| hydroxypropylmethylcellulose | 1.5 g |
| sodium hydroxide (1 N) | ad pH 5.0 |
| purified water | ad 100 g |

Method of Preparation

A mixture of phosphatidyl choline and cholesterol in ethyl alcohol is stirred and heated at 40° C. until complete solution. Ketoconazole microfine is dissolved in purified water by mixing while heating at 40° C. The alcoholic solution is added slowly to the aqueous solution while homogenizing during 10 minutes. Hydroxypropylmethylcellulose in purified water is added while mixing until swelling is complete. The resulting solution is adjusted to pH 5.0 with sodium hydroxide 1 N and diluted with the rest of the purified water.

Example 6

2% Scalp Lotion

| | |
|---|---|
| ketoconazole microfine | 20 mg |
| propylene carbonate | 241.4 mg |
| ethyl alcohol | 282.8 mg |
| purified water | q.s. ad 1 ml |

Method of Preparation

Ketoconazole microfine is stirred in a mixture of propylene carbonate and ethanol until completely dissolved. The resulting solution is diluted with purified water to the required concentration. The resulting solution is filled in appropriate bottles or in sprayers.

B. Clinical Example

Example 7

The utility of ketoconazole for treating alopecia can be demonstrated in the following test procedure. 27 Men (22–31 years) having androgenetic alopecia Hamilton Grade II used Nizoral® shampoo containing 2% ketoconazole during 60 weeks as often as shampooing was considered necessary by each individual. The frequency of shampooing varied between from 2 to 4 times weekly. Every 12 weeks trichograms were recorded on the hair of the areas on the periphery of the alopecia A hair index or pilary index $I_p$ was calculated by determining the proportion of hairs (A) (in %) in the anagen phase of the hair cycle and multiplying by the mean diameter (C) (in $\mu m$): $I_p = A \times C$. For adult individuals without androgenetic alopecia the $I_p$ value is higher than 60. In the 27 volunteers the mean $I_p$ value was 18 at the beginning of this test and did change little during the first 24 weeks of treatment A significant increase in the $I_p$ value according to the U-test ($p<0.05$) appeared at the 36th week. A net amelioration of the pilary index was observed in the course of the treatment reaching approximately twice its initial value after 60 weeks of treatment. These results indicate that ketoconazole does have a beneficial effect in alopecia and improving the overall quality of hair.

What is claimed is:

1. A method of treating individuals suffering from alopecia, said method comprising topically administering to said individuals to the affected areas of the scalp or beard the compound ketoconazole or a pharmaceutically acceptable acid addition salt thereof, in an amount effective in reversing, arresting or retarding said alopecia.

2. A method of treating individuals having an inferior quality of hair, said method comprising topically administering to the affected areas of the scalp or beard of said individuals the compound ketoconazole or a pharmaceutically acceptable acid addition salt thereof, in an amount effective in ameliorating the quality of hair.

3. The method of claim 1 wherein the ketoconazole is administered in a lotion comprising a dermatologically acceptable liquid carrier and, as active ingredient, ketoconazole in an amount effective in reversing, arresting or retarding alopecia.

4. The method of claim 2 wherein the ketoconazole is administered in a lotion comprising a dermatologically acceptable liquid carrier and, as active ingredient, ketoconazole in an amount effective in ameliorating the quality of hair.

5. The method of claim 3 wherein the lotion comprises from 0.1% to 5% (weight by volume) of ketoconazole.

6. The method of claim 4 wherein the lotion comprises from 0.1% to 5% (weight by volume) of ketoconazole.

7. The method of claim 1 wherein the ketoconazole is administered in a shampoo.

8. The method of claim 2 wherein the ketoconazole is administered in a shampoo.

* * * * *